US00PP17251P2

(12) United States Plant Patent
Hansen

(10) Patent No.: US PP17,251 P2
(45) Date of Patent: Nov. 28, 2006

(54) *HOSTA* PLANT NAMED 'RAINBOW'S END'

(50) Latin Name: *Hosta hybrida*
Varietal Denomination: Rainbow's End

(75) Inventor: Hans Andrew Hansen, Waseca, MN (US)

(73) Assignee: Shady Oaks Nursery, LLC, Waseca, MN (US)

( * ) Notice: Subject to any disclaimer, the term of this patent is extended or adjusted under 35 U.S.C. 154(b) by 0 days.

(21) Appl. No.: 11/238,466

(22) Filed: Sep. 29, 2005

(51) Int. Cl.
*A01H 5/00* (2006.01)

(52) U.S. Cl. ..... Plt./353

(58) Field of Classification Search ..... Plt./353
See application file for complete search history.

(56) References Cited

PUBLICATIONS http://www.plantdelights.com/Catalog/Spring/Detail/06035.html.*

* cited by examiner

*Primary Examiner*—Wendy Haas
(74) *Attorney, Agent, or Firm*—Penny J. Aguirri

(57) ABSTRACT

A new cultivar of *Hosta* named 'Rainbow's End', a sport of *Hosta* 'Obsession', that is characterized by its unique variegated foliage with dark green margins comprising about one third of the leaf area and centers that emerge yellow green and turn creamy white. 'Rainbow's End' is a medium sized *Hosta* with a mounded plant habit and pale violet flowers held above the foliage in late summer.

2 Drawing Sheets

Botanical classification: *Hosta hybrida.*
Cultivar designation: 'Rainbow's End'.

BACKGROUND OF THE INVENTION

The present invention, *Hosta* 'Rainbow's End', relates to a new and distinct cultivar of *Hosta*, botanically known as a *Hosta hybrida*, hereinafter referred to as 'Rainbow's End'.

The inventor discovered the new cultivar, 'Rainbow's End', in summer of 2000 in a tissue culture lab in Waseca, Minn. 'Rainbow's End' originated as a naturally occurring sport of *Hosta* 'Obsession' (unpatented). 'Rainbow's End' is unique in having variegated foliage with dark green margins and creamy white centers. The parent plant 'Obession' is variegated with dark green margins and medium green centers.

Asexual reproduction of the new cultivar was first accomplished by the inventor utilizing *in vitro* propagation in Waseca, Minn. in fall of 2002. Asexual reproduction of the new cultivar by division and tissue culture has shown that the unique features of 'Rainbow's End' are stable and reproduced true to type in successive generations.

SUMMARY OF THE INVENTION

The following traits have been repeatedly observed in trials in Minnesota for a period of five years and represent the characteristics of the new cultivar. These attributes in combination distinguish 'Rainbow's End' as a new and unique cultivar of *Hosta.*

1. The foliage of 'Rainbow's End' is variegated with dark green margins and centers that emerge yellow-green and mature to creamy white, margin width comprises on average about one third of the leaf area. The foliage of the parent plant, 'Obsession', has dark green margins and medium green centers and variegation that is much less pronounced than that of 'Rainbow's End'.

2. 'Rainbow's End' is a medium sized *Hosta* with a mounded plant habit, reaching a height of about 28 cm (exclusive of flower scapes) and a spread of about 53 cm in six years.
3. 'Rainbow's End' blooms in late summer with pale violet flowers that arise above the foliage from mid to late August in Minnesota.

BRIEF DESCRIPTION OF THE DRAWING

The accompanying colored photographs illustrate the overall appearance and distinct characteristics of the new *Hosta*. The photographs in the figures were taken in July of mature plants of 'Rainbow's End' and 'Obsession' as grown outdoors in Waseca, Minn. under the same conditions for five years.

Figure 1:
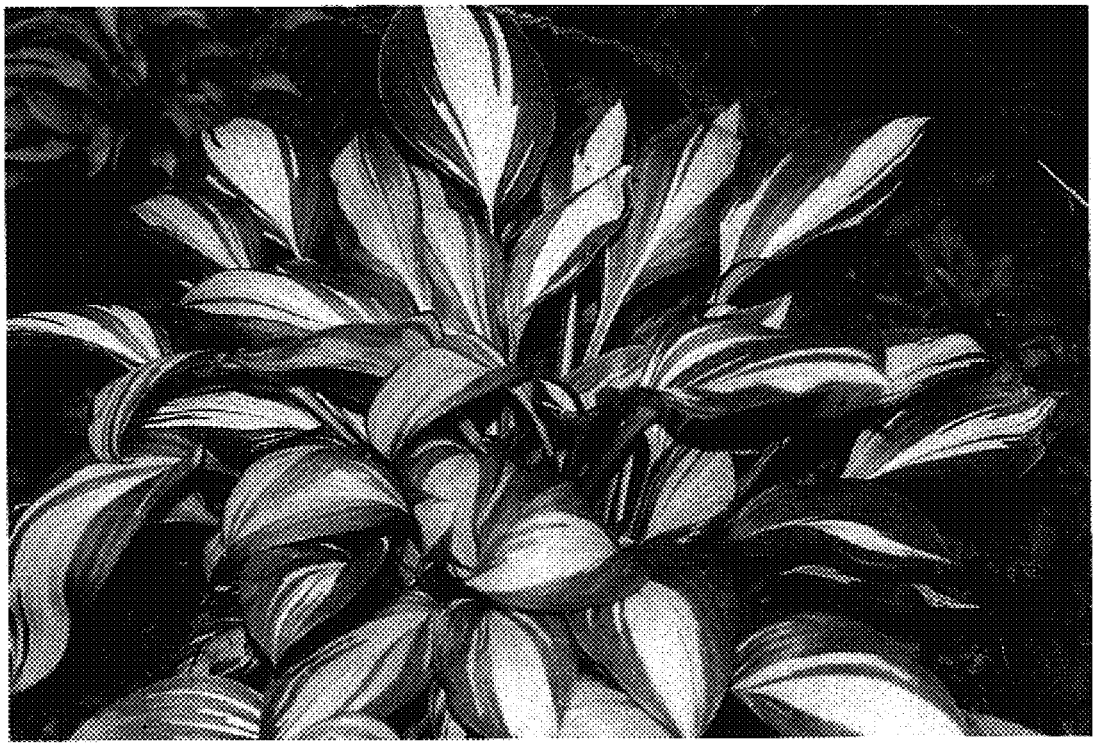
FIG. 1 provides an overall view of the plant habit and the foliage of the new cultivar, 'Rainbow's End'.
Figure 2:
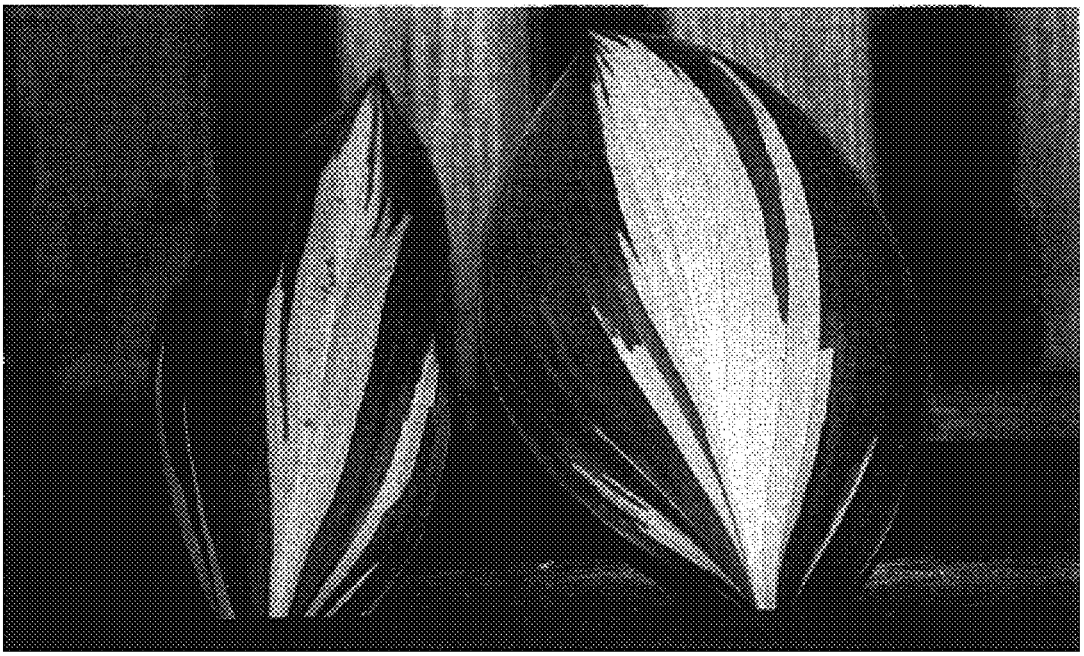
FIG. 2 provides a comparison of leaves of 'Rainbow's End'; a leaf of newly emerging foliage (spring foliage) on the left and a leaf of mature foliage (summer foliage) on the right.
Figure 3:
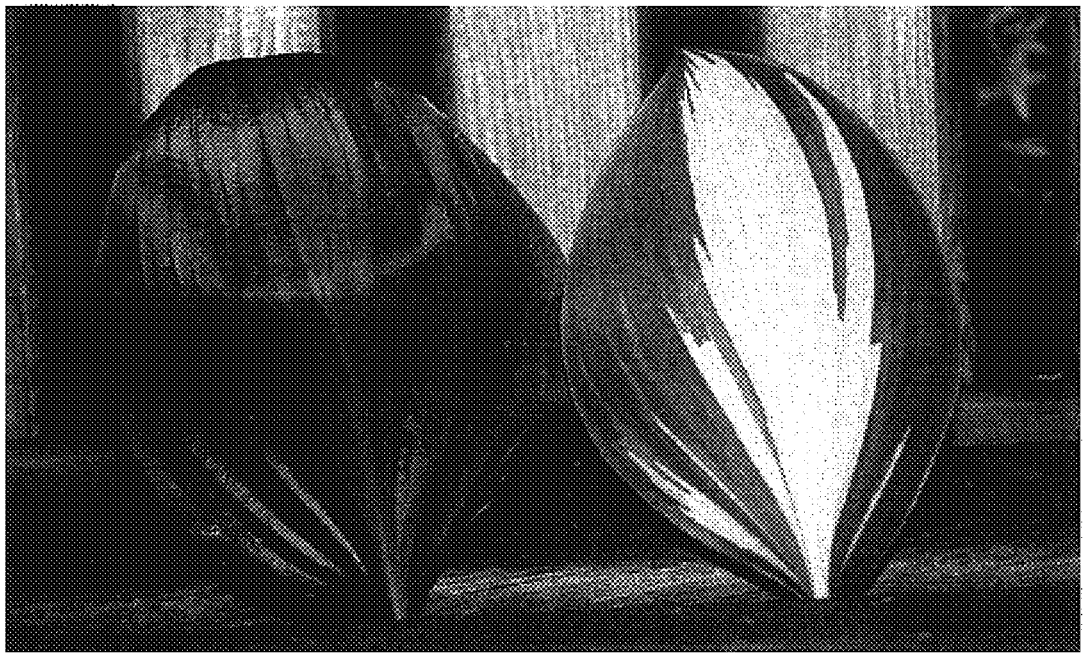
FIG. 3 provides a comparison between a leaf of 'Rainbow's End' (shown on right) and 'Obsession' (shown on left).

The colors in the photographs are as close as possible with the photographic and printing technology utilized and combined with the color values cited in the detailed botanical description accurately describe the colors of the new *Hosta.*

DETAILED BOTANICAL DESCRIPTION OF THE PLANT

The following is a detailed description of five year-old plants of the new cultivar as grown outdoors in Waseca, Minn. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

Botanical classification: 'Obsession' sport is a cultivar of *Hosta hybrida*.

Parentage: Sport of *Hosta* 'Obsession'.

General description:

*Blooming period.*—About 3 weeks, typically from about August 5 to August 25 in Minnesota.

*Plant habit.*—Herbaceous perennial, clump-forming, mounded habit, medium sized *Hosta*.

*Height and spread.*—Reaches about 28 cm (11 in) in height and about 53 cm (21 in) in width.

*Hardiness.*—U.S.D.A. Zones 3 to 8.

*Culture.*—Light to full shade, moist soils of moderate fertility.

*Diseases and pests.*—No susceptibility or resistance to diseases or other pests has been observed for 'Rainbow's End'.

*Root description.*—Freely branched, fleshy.

*Propagation.*—*In vitro* propagation is the preferred method utilizing typical methods for *Hosta*, division is also possible.

*Root development.*—Rooted transplants from tissue culture fully develop in a 96-cell liner in about 6 to 8 weeks in a greenhouse with average temperatures of about 70° F.

*Growth rate.*—Moderate.

Foliage description:

*Leaf shape.*—Elliptic.

*Leaf division.*—Simple.

*Leaf base. Rounded.*

*Leaf apex.*—Acuminate to cuspidate.

*Leaf aspect.*—Flat with tips slightly curled downward.

*Leaf venation.*—About 8 pairs of veins, campylodrome pattern, impressed on upper surface and raised on lower surface, color matches foliage coloration.

*Leaf margins.*—Entire.

*Leaf attachment.*—Petiolate.

*Leaf arrangement.*—Basal, radiate sprially from base.

*Leaf surface.*—Shiny on both surfaces of spring foliage, glabrous on uppr surface and slightly shiny on lower surface of summer foliage.

*Leaf substance.*—Average.

*Leaf variegation pattern.*—Dark green margins, yellow-green centers in spring that turn to creamy white in summer.

*Leaf color.*—Spring foliage upper surface; margins color between 137A and 139A, centers 144C and changing to 144D. Spring foliage lower surface; margins 137A, centers color between 144C and 1344D. Summer foliage upper surface; margins color between 137A and 139A, centers 158B. Summer foliage lower surface; margins 137B, centers 158A, intermediate area between margins and centers 138B.

*Leaf size.*—Average of 15 cm in length, average of 10 cm in width.

*Leaf quantity.*—About 5 to 7 per shoot (eye).

*Petiole size.*—About 17 cm in length, average 7 mm in width.

*Petiole color.*—Inner surface; variegated with stripes of 137A and 144C to 144D, outer surface; narrow stripes near margin of 137A and centers 144C with small flecks of N77B.

*Petiole surface.*—Slightly shiny on inner surface, glaucous on outer surface.

*Petiole shape.*—Sulcate.

Flower scape description:

*Scape shape.*—Round, solid.

*Scape number.*—One per mature eye under normal growing conditions.

*Scape posture.*—Straight, held upright at about 80 to 90° from vertical.

*Scape size.*—About 40 to 48 cm in length, about 4 mm in width.

*Scape color.*—139D heavily speckled with 59B.

*Scape surface.*—Glabrous.

*Leaf bracts.*—About 2, about 3 cm in length and 1.2 cm in width, papery, lanceolate in shape, 158C in color blushed N77C with and thin lines of N77C, dry to 162A.

Flower description:

*Inflorescence type.*—Terminal racemes of single tubular-shaped flowers.

*Lastingness of inflorescence.*—About 3 weeks from first opening bloom to fading of last opening bloom, individual blooms last about one day.

*Flower shape.*—Tubular.

*Flower number.*—About 15 to 20.

*Flower internode length.*—Average of 1 cm.

*Flower fragrance.*—None.

*Flower bud shape.*—Spathulate.

*Flower bud size.*—Up to about 3.5 cm in length and 1.2 cm in diameter.

*Flower bud color.*—85D blushed with 85C.

*Flower size.*—About 4.5 cm in length and 2.5 cm in diameter.

*Flower color.*—85C (and slightly lighter) to 85D.

*Pedicels.*—About 7 mm in length and 2 mm in diameter, 85D in color.

*Perianth features.*—Compound of 6 tepals, 3 interior and 3 exterior, fused in tube region and about one third of expanded region then overlapping towards apex.

*Tepal shape.*—Spatulate.

*Tepal size.*—About 4 cm in length, up to 1 cm in width.

*Tepal color.*—Inner and outer surface 85D with shading of 85C.

*Tepal texture.*—Glabrous.

*Floral bracts.*—1 per flower, lanceolate in shape, papery, 158C in color blushed and thin lines of N77C, about 2 cm in length and 8 mm in width.

Reproductive organs:

*Gynoecium.*—1 Pistil. Style is about 3.5 cm in length, 0.7 mm in width and 155B in color. Stigma is 3-lobed, 14A in color and 0.75 mm in diameter. Ovary is superior, compound, composed of 3 locules, oblong in shape, 5 mm in length, 3 mm in width and 144D in color.

*Androecium.*—6 stamens, filament is 155B in color, about 4 cm in length, 0.7 mm in width, curved inward and not extending beyond perianth, anthers are 3 mm in length, 1.5 mm in width, attachment is versatile, 202A in color, dehiscence is longitudinal, pollen is abundant and 15B in color.

*Fruit.*—Fruit set was not observed under the conditions tested.

I claim:

1. A new and distinct cultivar of *Hosta* plant named 'Rainbow's End' as herein illustrated and described.

* * * * *